(12) United States Patent
Tong et al.

(10) Patent No.: US 11,751,791 B2
(45) Date of Patent: Sep. 12, 2023

(54) ECG MEASUREMENT MODE SWITCHING BASED ON POSITION ON BODY

(71) Applicant: GOERTEK INC., Shandong (CN)

(72) Inventors: Ziwei Tong, Shandong (CN); Xiao Bao, Shandong (CN)

(73) Assignee: GOERTEK INC., Shandong (CN)

(*) Notice: Subject to any disclaimer, the term of this patent is extended or adjusted under 35 U.S.C. 154(b) by 0 days.

(21) Appl. No.: 17/594,993

(22) PCT Filed: Dec. 27, 2019

(86) PCT No.: PCT/CN2019/129303
§ 371 (c)(1),
(2) Date: Nov. 4, 2021

(87) PCT Pub. No.: WO2021/082259
PCT Pub. Date: May 6, 2021

(65) Prior Publication Data
US 2022/0142547 A1    May 12, 2022

(30) Foreign Application Priority Data
Oct. 29, 2019    (CN) .......................... 201911039165.9

(51) Int. Cl.
*A61B 5/318*    (2021.01)
*A61B 5/0205*    (2006.01)
(Continued)

(52) U.S. Cl.
CPC ............ *A61B 5/318* (2021.01); *A61B 5/0205* (2013.01); *A61B 5/0245* (2013.01);
(Continued)

(58) Field of Classification Search
None
See application file for complete search history.

(56) References Cited

U.S. PATENT DOCUMENTS

| 2008/0221410 A1* | 9/2008 | Campbell ............ G01N 21/474 600/323 |
| 2009/0182205 A1* | 7/2009 | Cho ..................... A61B 5/0261 600/372 |

(Continued)

FOREIGN PATENT DOCUMENTS

| CN | 101772320 A | 7/2010 |
| CN | 102085090 A | 6/2011 |

(Continued)

OTHER PUBLICATIONS

International Search Report, English Translation, dated Jul. 29, 2020, from PCT/CN2019/129303 filed Dec. 27, 2019.

(Continued)

*Primary Examiner* — Lynsey C Eiseman
*Assistant Examiner* — James Moss
(74) *Attorney, Agent, or Firm* — HAUPTMAN HAM, LLP

(57) ABSTRACT

A method and an apparatus for switching an ECG measurement mode, a wearable device, and a computer-readable storage medium. The method includes: receiving two successive pieces of PPG data transmitted by an optical heart-rate sensor, where the PPG data is generated by a contact between a measurement electrode and a skin; calculating a difference between the two received pieces of the PPG data; and controlling switching among measurement modes based on the difference, where the measurement modes comprise an ECG wristband mode and an ECG chest-lead mode Manual switching of an ECG measurement mode is avoided with simple operations, high efficiency, and more intelligence.

17 Claims, 4 Drawing Sheets

(51) Int. Cl.
*A61B 5/024* (2006.01)
*A61B 5/0245* (2006.01)
*A61B 5/00* (2006.01)

(52) U.S. Cl.
CPC ........ *A61B 5/02416* (2013.01); *A61B 5/6823* (2013.01); *A61B 5/6833* (2013.01)

(56) References Cited

U.S. PATENT DOCUMENTS

| | | | |
|---|---|---|---|
| 2010/0081913 A1* | 4/2010 | Cross | A61B 5/282 600/509 |
| 2010/0188231 A1 | 7/2010 | Winter et al. | |
| 2011/0128499 A1 | 6/2011 | Endo et al. | |
| 2011/0137133 A1 | 6/2011 | Espina Perez | |
| 2011/0245622 A1* | 10/2011 | McKenna | G16H 40/63 600/300 |
| 2014/0153610 A1 | 6/2014 | Shih et al. | |
| 2014/0197965 A1* | 7/2014 | Park | A61B 5/02055 340/870.09 |
| 2015/0351690 A1* | 12/2015 | Toth | A61B 5/14517 600/391 |
| 2015/0366469 A1* | 12/2015 | Harris | A61B 5/318 600/301 |
| 2016/0245766 A1 | 8/2016 | Nelson et al. | |
| 2017/0224263 A1* | 8/2017 | Lobbestael | A61B 5/684 |
| 2017/0281027 A1 | 10/2017 | Altmejd et al. | |
| 2018/0035943 A1* | 2/2018 | Shemesh | A61B 5/7203 |
| 2018/0042502 A1 | 2/2018 | Wang et al. | |
| 2019/0209045 A1 | 7/2019 | Gelissen et al. | |
| 2021/0186420 A1* | 6/2021 | Lee | A61B 5/282 |

FOREIGN PATENT DOCUMENTS

| | | |
|---|---|---|
| CN | 102123656 A | 7/2011 |
| CN | 103385702 A | 11/2013 |
| CN | 103845041 A | 6/2014 |
| CN | 104207755 A | 12/2014 |
| CN | 107260150 A | 10/2017 |
| CN | 107277266 A | 10/2017 |
| CN | 107714024 A | 2/2018 |
| CN | 107925488 A | 4/2018 |
| CN | 108024745 A | 5/2018 |
| CN | 108937914 A | 12/2018 |
| CN | 109640793 A | 4/2019 |
| CN | 110680306 B | 11/2020 |
| KR | 20070060308 A | 6/2007 |
| WO | 2011132117 A1 | 10/2011 |
| WO | 2017053925 A1 | 3/2017 |

OTHER PUBLICATIONS

The State Intellectual Property Office of People's Republic of China, Notification to Grant Patent Right for Invention, dated Nov. 4, 2020, for Chinese Patent Application No. 201911039165, filed Oct. 29, 2019.
China National Intellectual Property Agency, Notification of the First Office Action, dated May 28, 2020, for Chinese Patent Application No. 201911039165, filed Oct. 29, 2019.

* cited by examiner

ECG MEASUREMENT MODE SWITCHING BASED ON POSITION ON BODY

The present application is the national phase of International Application No. PCT/CN2019/129303, titled "ECG ELECTROCARDIOGRAPHIC MEASUREMENT MODE SWITCHING METHOD AND APPARATUS, AND WEARABLE DEVICE AND STORAGE MEDIUM", filed on Dec. 27, 2019, which claims priority to Chinese Patent Application No. 201911039165.9, titled "METHOD AND APPARATUS FOR SWITCHING ECG MEASUREMENT MODE, WEARABLE DEVICE AND STORAGE MEDIUM", filed on Oct. 29, 2019 with the China National Intellectual Property Agency, which is incorporated herein by reference in its entirety.

FIELD

The present disclosure relates to the field of intelligent wearable technology, and in particular to a method and an apparatus for switching an ECG (electrocardiogram) measurement mode, a wearable device, and a computer-readable storage medium.

BACKGROUND

At present, many smart watches have an ECG (electrocardiogram) measurement function, that is, a function of measuring a heart rate of a user in real time, drawing an ECG of the user simultaneously, and displaying the ECG on a corresponding application. Generally, there are two modes of ECG measurement, i.e. a wristband mode and a chest-lead mode. In the wristband mode, the smart watch is wore on the wrist, and a measurement electrode located at a back of a case of the smart watch is pressed against the skin, so that an ECG chip in the smart watch is capable of measuring a bioelectric signal generated by the heart, to obtain an ECG. In the chest-lead mode, an external auxiliary device connected to the case of the smart watch is attached to a designated position on the chest, a measurement electrode is in full contact with the skin, and ECG data can be recorded all day long. Generally, a conventional smart watch is switched between ECG measurement modes in two manners. In a first manner, the ECG measurement mode is switched from one to another via a physical button (or a touch screen) of the smart watch. In a second manner, the ECG measurement mode is selected in an application, and a message is sent to the smart watch for mode selection. In the above two manners, the ECG measurement mode is manually switched, which is slow and inconvenience. A method for automatically switching the ECG measurement mode is required in view of such issue Therefore, there is a need for those skilled in the art to provide a solution that addresses the above technical issue.

SUMMARY

An objective of the present disclosure is to provide a method and an apparatus for switching an ECG measurement mode, a wearable device, and a computer-readable storage medium. The method for switching an ECG (electrocardiogram) measurement mode is simple and efficient. The solutions are as follows.

A method for switching an ECG measurement mode is provided according to embodiments of the present disclosure. The method includes: receiving two successive pieces of PPG data transmitted by an optical heart-rate sensor, where the PPG data is generated by a contact between a measurement electrode and a skin; calculating a difference between the two received pieces of the PPG data; and controlling switching among measurement modes based on the difference, where the measurement modes include an ECG wristband mode and an ECG chest-lead mode.

In an optional embodiment, before controlling the switching among the measurement modes based on the difference, the method further includes: determining whether an absolute value of the difference is greater than or equal to a predetermined threshold.

In an optional embodiment, receiving the two successive pieces of the PPG data transmitted by the optical heart-rate sensor includes: detecting, via an ECG chip, a state of the contact between the measurement electrode and the skin; and obtaining, based on the state of the contact, the two successive pieces of the PPG data transmitted by the optical heart-rate sensor.

In an optional embodiment, calculating the difference between the two received pieces of the PPG data includes: obtaining two averages based on the two received pieces, respectively, of the PPG data; and calculating a difference between the two averages as the difference between the two pieces of the PPG data.

In an optional embodiment, obtaining, based on the state of contact, the two successive pieces of the PPG data transmitted by the optical heart-rate sensor includes: determining whether a piece of the PPG data being collected when the measurement electrode is detached from the skin is complete; determining a piece of the PPG data received before the measurement electrode is detached from the skin as the a preceding one of the two pieces of the PPG data, in response to the piece of the PPG data being collected when the measurement electrode is detached from the skin being not complete; and acquiring a succeeding one of the two pieces of the PPG data when the measurement electrode is re-attached to the skin.

In an optional embodiment, after controlling the switching among the measurement modes based on the difference, the method further includes: transmitting a current one of the measurement modes to a display device, to prompt a user that the switching is completed.

An apparatus for switching an ECG measurement mode is provided according to the embodiments of the present disclosure. The apparatus includes: a PPG data acquisition module, configured to receive two successive pieces of PPG data transmitted by an optical heart-rate sensor, where the PPG data is generated by a contact between a measurement electrode and a skin; a difference calculation module, configured to calculate a difference between the two received pieces of the PPG data; and a switching module, configured to control switching among measurement modes based on the difference, where the measurement modes include an ECG wristband mode and an ECG chest-lead mode.

A wearable device is provided according embodiments of the present disclosure. The wearable device includes: an optical heart-rate sensor, configured to collect, at a preset sampling frequency, two successive pieces of PPG data generated by a contact between a measurement electrode and a skin; an ECG chip, configured to measure electrophysiological signals in an ECG wristband mode and in an ECG chest-lead mode, to monitor a heart rate; a memory, configured to store a computer program; and an MCU, configured to perform the forgoing method for switching the ECG measurement mode when executing the computer program.

In an embodiment, the ECG chip is further configured to: transmit a detachment signal to the MCU, in response to detecting an electrical signal indicating that the measurement electrode is detached from the skin; and transmit an attachment signal to the MCU, in response to detecting an electrical signal indicating that the measurement electrode is re-attached to the skin.

A computer-readable storage medium is provided according to embodiments of the present disclosure. The computer-readable storage medium stores a computer program that, when executed by a processor, implements the foregoing method for switching the ECG measurement mode.

The method for switching the ECG measurement mode is provided according to embodiments of the present disclosure. The method includes: receiving the two successive pieces of the PPG data transmitted by the optical heart-rate sensor, where the PPG data is generated by the contact between the measurement electrode and the skin; calculating the difference between the two received pieces of the PPG data; and controlling the switching among the measurement modes based on the difference, where the measurement modes include the ECG wristband mode and the ECG chest-lead mode.

According to embodiments of the present disclosure, the optical heart-rate sensor collects the two successive pieces of the PPG data generated by the contacts between the measurement electrode and the skin, the difference between such two pieces of the PPG data is calculated, and the switching among the measurement modes is controlled based on the difference. Hence, manual switching of an ECG measurement mode is avoided with simple operations, high efficiency, and more intelligence.

The apparatus for switching an ECG measurement mode, the wearable device, and the computer-readable storage medium are further provided according to embodiments of the present disclosure. The above beneficial effects also apply to the apparatus, the wearable device and the computer-readable storage medium, and are not repeated herein.

BRIEF DESCRIPTION OF THE DRAWINGS

For clearer illustration of the technical solutions according to embodiments of the present disclosure or conventional techniques, hereinafter briefly described are the drawings to be applied in embodiments of the present disclosure or conventional techniques. Apparently, the drawings in the following descriptions are only some embodiments of the present disclosure, and other drawings may be obtained by those skilled in the art based on the provided drawings without creative efforts.

DETAILED DESCRIPTION OF EMBODIMENTS

Hereinafter technical solutions in embodiments of the present disclosure are described clearly and completely in conjunction with the drawings in embodiments of the present closure. Apparently, the described embodiments are only some rather than all of the embodiments of the present disclosure. Any other embodiments obtained based on the embodiments of the present disclosure by those skilled in the art without any creative effort fall within the scope of protection of the present disclosure.

Figure 1:
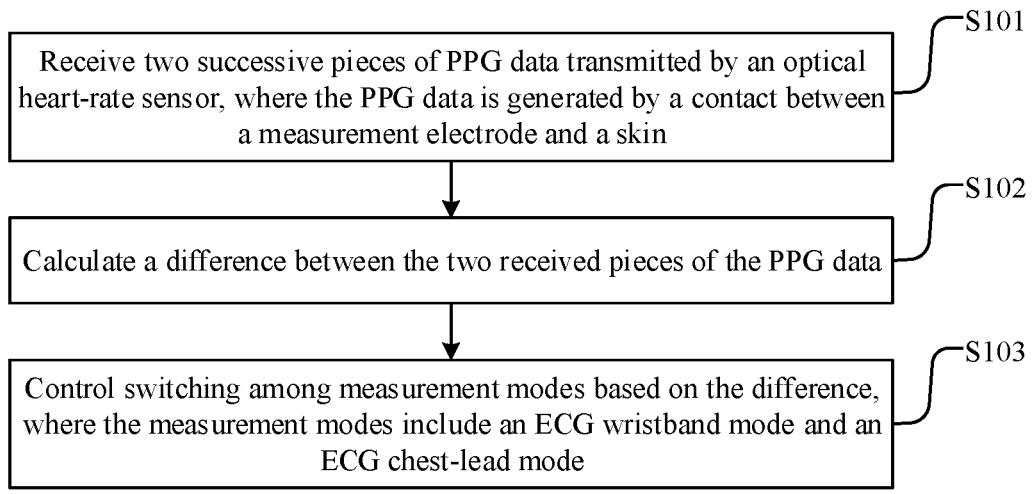
FIG. 1 is a flowchart of a method for switching an ECG (electrocardiogram) measurement mode according to an embodiment of the present disclosure.

Switching among ECG measurement modes is manually implemented in conventional technology, which is troublesome and inefficient. In view of the above technical issue, a method for switching an ECG measurement mode is provided according to an embodiment of the present disclosure. The switching is implemented with simplicity and high efficiency. Reference is made to FIG. 1, which is a flowchart of a method for switching an ECG measurement mode according to an embodiment of the present disclosure. The method includes following steps S101 to S103.

In step S101, two successive pieces of PPG data transmitted by an optical heart-rate sensor are received, where the PPG data is generated by a contact between a measurement electrode and a skin.

In this embodiment, photoplethysmography (PPG) is a technique of inducing a light into a skin and measuring light scattered due to a blood flow. In a specific embodiment, an LED in the optical heart-rate sensor emits a light that is incident on the skin, the reflected light travels through tissues in the skin, and a photosensitive sensor receives a reflected light and converts the reflected light into an electrical signal. The electrical signal is converted into a digital signal through analogy-digital conversion. Thereby, the PPG data for measuring a heart rate is generated, and a PPG waveform is acquired based on multiple pieces of the PPG data. The light, which is emitted from the LED in the optical heart-rate sensor and incident on the skin, travels through the skin and is then reflected to the photosensitive sensor. In such process, the light is subject to attenuation. A first measured part of a body may be not under significant movement, for example, a muscle, a bone, a vein, or another conjunctive tissue. In such case, absorption of the light is basically unchanged, and hence a DC (direct current) component is significant while an AC (alternative current) component is small in a collected signal. In comparison, a second measured part of the body may have a fast blood flow, for example, a part with many arteries, such as the chest. In such case, the absorption of the light varies greatly at such part. The DC component in the collected signal differs little in comparison with that in the former case, but the AC component would be great. Hence, a signal at the first measured part would be quite different from that at the second measured part, and accordingly the PPG data obtained at the first measured part would be quite different from that obtained at the second measured part. The PPG data may be used to learn which part the measurement electrode is in contact with.

Each PPG waveform is drawn based on PPG data collected at a predetermined frequency within a predetermined period of time. Generally, a horizontal axis represents sampling points and a vertical axis represents amplitude. It can be understood that the amplitude of PPG data obtained from measurement at the wrist is smaller than that obtained from measurement at the chest. In this step, two successive pieces of the PPG data transmitted by the optical heart-rate sensor are received. In a first embodiment, the preceding piece (the first piece) of the PPG data generated by the contact with the skin is the PPG data at a first part, and the succeeding piece (the second piece) of the PPG data generated by the contact with the skin is another PPG data at the first part. The first part may be the wrist or the chest. In a second embodiment, the preceding piece (the first piece) of the PPG data generated by the contact with the skin is the PPG data at a first part, and the succeeding piece (the second piece) of the PPG data generated by the contact with the skin is the PPG data at a second part. The first part is the wrist and the second part is the chest, or the first part is the chest and the second part is the wrist.

In this embodiment, a manner of collecting the two pieces of the PPG data is not limited. The PPG data may be collected according to a predetermined rule. For example, the PPG data may be periodically collected at a predetermined interval, or the PPG data may be collected in response to reading a collection instruction, or the PPG data may be collected at predetermined moments. The manner of collecting the PPG data may be customized, as along as an objective of this embodiment can be achieved. For example, a group of the PPG data is collected as a piece of PPG data at an interval of 10 minutes. Alternatively, a group of PPG data is collected as a piece of the PPG data in response to reading the collection instruction. Alternatively, a group of PPG data is collected as a piece of the PPG data in response to reading an attachment signal (which is triggered when the measurement electrode is re-attached to the skin after being detached from the skin). Alternatively, groups of PPG data are collected at 12:00, 12:30, and 12:40, respectively.

In step S102, a difference between the two received pieces of the PPG data is calculated.

In this embodiment, a quantity of sampling points for the PPG data is not limited. It can be understood that a sampling frequency and the quantity of sampling points are identical in the two pieces of the PPG data. A manner of calculating the difference is not limited in this embodiment. The difference may be calculated by subtracting a sum of the amplitude in one piece of the PPG data from a sum of the amplitude in the other piece of the PPG data. Alternatively, the difference may be calculated by subtracting an average of the amplitude in one piece of the PPG data from an average of the amplitude in the other piece of the PPG data. The manner of calculating the difference may be customized. The difference may be calculated by subtracting a value corresponding to the succeeding piece of the PPG data from a value corresponding to the preceding piece of the PPG data. Alternatively, the difference may be calculated by subtracting a value corresponding to the preceding piece of the PPG data from a value corresponding to the succeeding piece of the PPG data. The difference may be positive or negative.

In step S103, switching among measurement modes is controlled based on the difference. The measurement modes include an ECG wristband mode and an ECG chest-lead mode.

In this embodiment, the ECG is measured through electrical potentials, that is, through electrocardiography. The electrocardiography for obtaining the ECG has the ECG wristband mode and the ECG chest-lead mode when being applied to the wrist and the chest, respectively. The automatic switching between the two modes is performed based on the PPG data obtained through the PPG technique. In brief, the PPG data acquired at such two parts of the body are different because the characteristics of such two parts are different, and hence the switching between the two modes is performed based on the difference between the two received pieces of the PPG data.

In one embodiment, a measurement mode is maintained in response to an absolute value of the difference being less than a predetermined threshold.

As a first example, a current measurement mode is the ECG chest-lead mode, and the absolute value of the difference is less than the predetermined threshold. Hence, the measurement mode is kept to be the chest-lead mode.

As a second example, a current measurement mode is the ECG wristband mode, and the absolute value of the difference is less than the predetermined threshold. Hence, the measurement mode is kept to be the wristband mode.

In another embodiment, one of the ECG chest-lead mode and the ECG wristband mode is controlled to be switched to the other, in response to an absolute value of the difference is greater than or equal to a predetermined threshold.

As a first example, a current measurement mode is the ECG wristband mode, and the difference is greater than or equal to the predetermined threshold. Specifically, the absolute value of the difference a3 obtained by subtracting the succeeding piece a2 of the PPG data from the preceding piece a1 of the PPG data is greater than or equal to the predetermined threshold T. Here the succeeding piece a2 of the PPG data is collected at the chest, which has a fast blood flow, and there is a2≥a1. In such case, the current measurement mode is switched from the ECG wristband mode to the ECG chest-lead mode.

As a second example, a current measurement mode is the ECG chest-lead mode, and the difference is greater than or equal to the predetermined threshold. Specifically, the absolute value of the difference obtained by subtracting the succeeding piece b2 of the PPG data from the preceding piece b1 of the PPG data is greater than or equal to the predetermined threshold. In this case, the PPG data b2 received in the second reception is acquired in the wrist, and there is b1≥b2. In such case, the current measurement mode is switched from the ECG chest-lead mode to the ECG wristband mode.

In this embodiment, the PPG data is acquired through the PPG technique, and the difference between the two successive pieces of the PPG data generated by the contact between the measurement electrode and skin serves as a condition of switching the measurement mode. The automatic switching among the measurement modes is achieved, and the ECG is obtained based on measuring electrophysiological signals in electrocardiography.

Additionally, after the switching between the measurement modes is controlled based on the difference, the method further includes a following step. A current measurement mode is stored. The current measurement mode is stored each time the switching is performed.

Additionally, the method further includes a following step. The current measurement mode is transmitted to a display device, to prompt a user that the switching among ECG measurement modes is implemented.

Based on the above solution in this embodiment, the optical heart-rate sensor collects the two successive pieces of the PPG data generated by the contacts between the measurement electrode and the skin, the difference between such two pieces of the PPG data is calculated, and the switching among the measurement modes is controlled based on the difference. Hence, manual switching of an ECG measurement mode is avoided with simple operations, high efficiency, and more intelligence.

Figure 2:
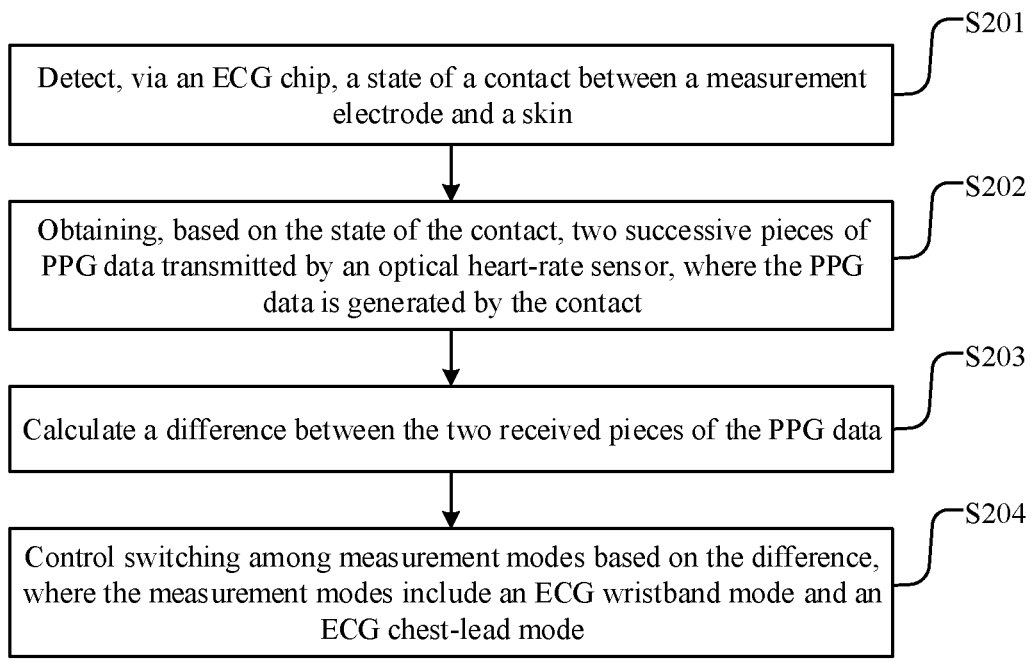
FIG. 2 is a flowchart of a method for switching an ECG measurement mode according to another embodiment of the present disclosure.

On a basis of the above embodiments, a method for switching an ECG measurement mode is provided according to an embodiment. Reference is made to FIG. 2, which is a flowchart of method for switching an ECG measurement mode according to another embodiment of the present disclosure. The method includes following steps S201 to S204.

In step S201, a state of a contact between a measurement electrode and a skin is detected via an ECG chip.

In step S202, two successive pieces of PPG data transmitted by the optical heart-rate sensor are obtained, where the PPG data is generated by the contact between the measurement electrode and the skin.

In this embodiment, the ECG chip determines the state of contact between the measurement electrode and the skin, and transmits a detachment signal to an MCU in response to the measurement electrode being detached from the skin. In a specific embodiment, when a watch is removed from the wrist or a chest electrode (which is an external auxiliary device connected to the watch in the chest-lead mode) is removed from the chest, the measurement electrode is no longer in contact with the skin. A bioelectric potential sensor on the ECG chip of the watch is not capable of detecting an electrical signal, and hence the ECG chip transmits to the MCU the detachment signal indicating such detachment from the skin. Additionally, after the detachment signal transmitted by the ECG chip is received, the method further includes a following step. A piece of the PPG data generated before the detachment from the skin is stored. When the measurement electrode is re-attached to the skin, the ECG chip transmits to the MCU an attachment signal indicating re-attachment to the skin, and the MCU recovers collecting the PPG data via the optical heart-rate sensor.

In step S203, a difference between the two received pieces of the PPG data is calculated.

Additionally, the step S203 includes following steps. Two averages are obtained based on the two received pieces, respectively, of the PPG data. A difference between the two averages is calculated as the difference between the two pieces of the PPG data.

It can be understood that the difference is calculated by subtracting an average of the amplitude in one piece of the PPG data from an average of the amplitude in another piece of the PPG data. The MCU acquires the preceding piece of the PPG data at a sampling rate via the optical heart-rate sensor of a wearable device, obtains a first average based on the preceding piece of the PPG data, and acquires a current measurement mode. An initial measurement mode of the wearable device is set to be a wristband mode by default, and the measurement mode is stored each time the switching has been performed. After the two averages corresponding to two received pieces of the PPG data are obtained, the difference is calculated based on the two averages, which reflects a change between the two pieces of the PPG data accurately. Accuracy is improved.

Additionally, obtaining the two successive pieces of the PPG data, which is transmitted by the optical heart-rate sensor and generated by the contact between the measurement electrode and the skin, based on the state of contact includes flowing steps. It is determined whether a piece of the PPG data being collected when the measurement electrode is detached from the skin is complete. In a case that such piece of the PPG data is not complete, a piece of the PPG data received before the measurement electrode is detached from the skin is determined as the preceding piece of the PPG data. The succeeding piece of the PPG data is acquired when the measurement electrode is re-attached to the skin.

In a case that the measurement electrode is detached from the skin when a piece of the PPG data is not completely acquired, such piece of the PPG data is not completely acquired or there is an error in the acquired piece of the PPG data. Therefore, in this embodiment, it is determined whether the piece of the PPG data being acquired when the measurement electrode is detached from the skin is complete. In case of positive determination, such piece of the PPG data serves as the preceding piece of the PPG data. In case of negative determination, the piece of the PPG data received before the measurement electrode is detached from the skin serves as the preceding piece of the PPG data. Integrity of such data is ensured, and hence data correctness can be ensured when calculating the difference between the preceding piece and the succeeding piece of the PPG data.

In step S204, the switching between measurement modes is controlled based on the difference. The measurement modes include an ECG wristband mode and an ECG chest-lead mode.

The MCU calculates a second average based on the succeeding piece of the PPG data, and then compares the second average with the first average. In a case that an absolute value of the difference is greater than a predetermined threshold, the measurement mode is switched and a new current measurement mode is stored. In a case that the absolute value of the difference is less than the predetermined threshold, the current measurement mode is maintained. The switching between the measurement modes includes switching from the ECG wristband mode to the ECG chest-lead mode, and switching from the ECG chest-lead mode to the ECG wristband mode.

Based on the above technical solutions of this embodiment, the PPG data is acquired based on the state of contact between the measurement electrode and the skin, which is detected by the ECG chip. Switching between the measurement modes is fast and efficient, and accuracy of the finally acquired ECG data is ensured.

Figure 3:
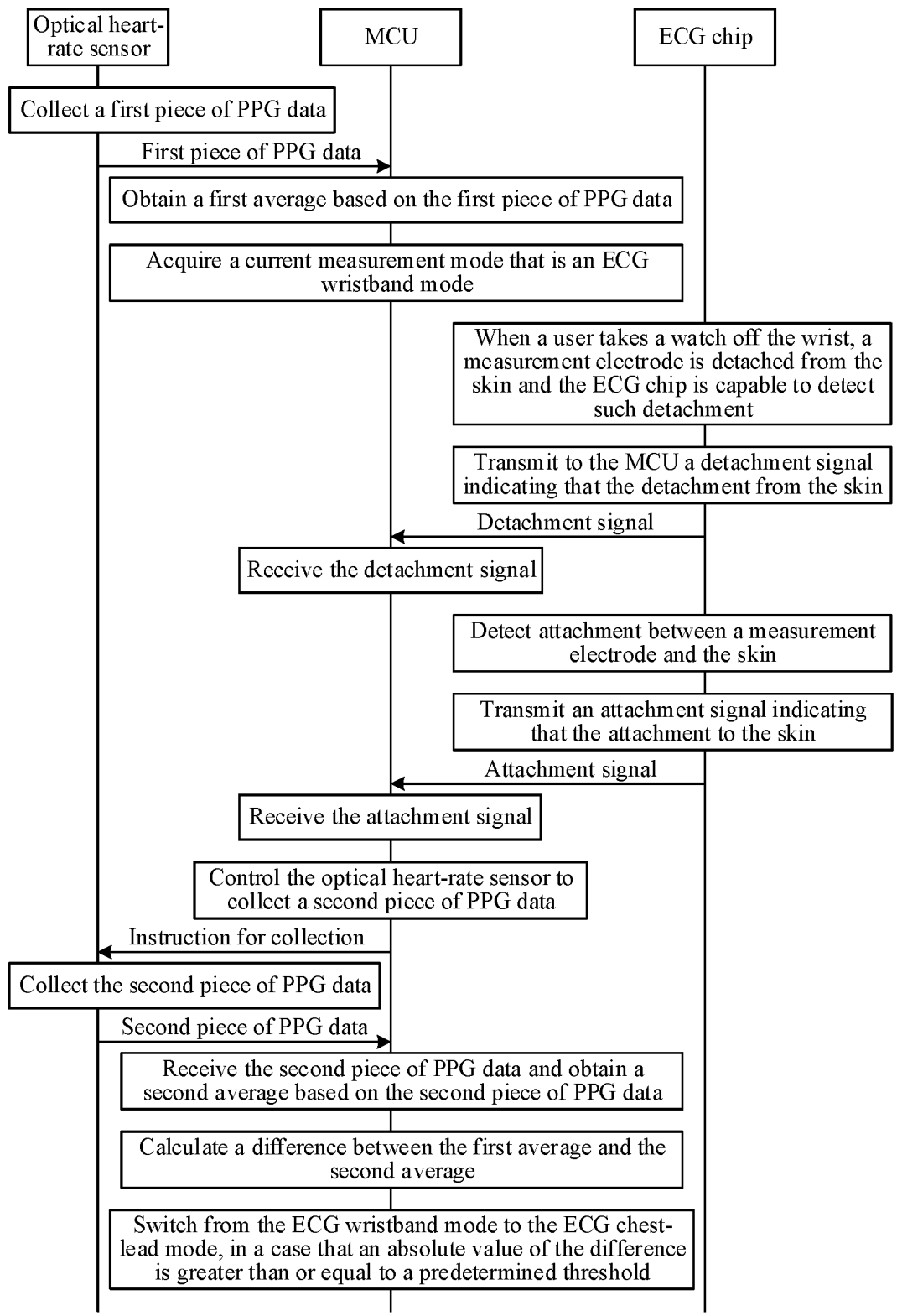
FIG. 3 is a flowchart of switching from an ECG wristband mode to an ECG chest-lead mode according to an embodiment of the present disclosure.

A method for switching from the ECG wristband mode to the ECG chest-lead mode is provided according to an embodiment of the present disclosure. Reference is made to FIG. 3, which is a flowchart of switching from an ECG wristband mode to an ECG chest-lead mode according to an embodiment of the present disclosure. The switching includes following steps.

In a case that a current measurement mode is the ECG wristband mode, the optical heart-rate sensor collects the preceding piece of the PPG data, and transmits the preceding piece of the PPG data to the MCU. The MCU obtains an average based on such piece of the PPG data, and further obtains the current measurement mode being the ECG wristband mode, due to previous storage of the current measurement mode. When a user takes the watch off the wrist, a measurement electrode is detached from the skin, and the ECG chip detects such detachment (a bioelectric potential sensor on the chip detects no electrical signal after the measurement electrode is detached from the skin, that is, there is no data). Then, the ECG chip transmits to the MCU a detachment signal indicating the detachment from skin. When an external auxiliary device attached to a heart location on the chest is connected to the watch, the ECG chip detects that a measurement electrode is attached to the skin, and the ECG chip transmits to the MCU an attachment signal indicating such re-attachment to the skin. The MCU controls the optical heart-rate sensor to collect the succeeding piece of the PPG data. The MCU receives the succeeding piece of the PPG data and calculates a corresponding average. A difference between the average obtained after the re-attachment and the previously acquired average is calculated. A tissue at the wrist has a structure significantly different from that of a tissue at the chest. Light absorption of muscles, bones, veins and other conjunctive tissues at the wrist is basically unchanged. That is, the DC component is significant, while the AC component is small. There are many arteries and a large blood flow at the chest, and hence light absorption of the chest varies with a large AC component. That is, the AC signal in the PPG data at the chest is larger than that at the wrist, and hence there is an obvious difference between the two averages corresponding to the PPG data at such two parts, respectively. In a specific embodiment, the difference between the two averages may be obtained. In a case that the absolute value of such difference is greater than the predetermined threshold, the measurement mode is switched to the chest-lead mode, and the chest-lead mode is stored as the current measurement mode.

Figure 4:
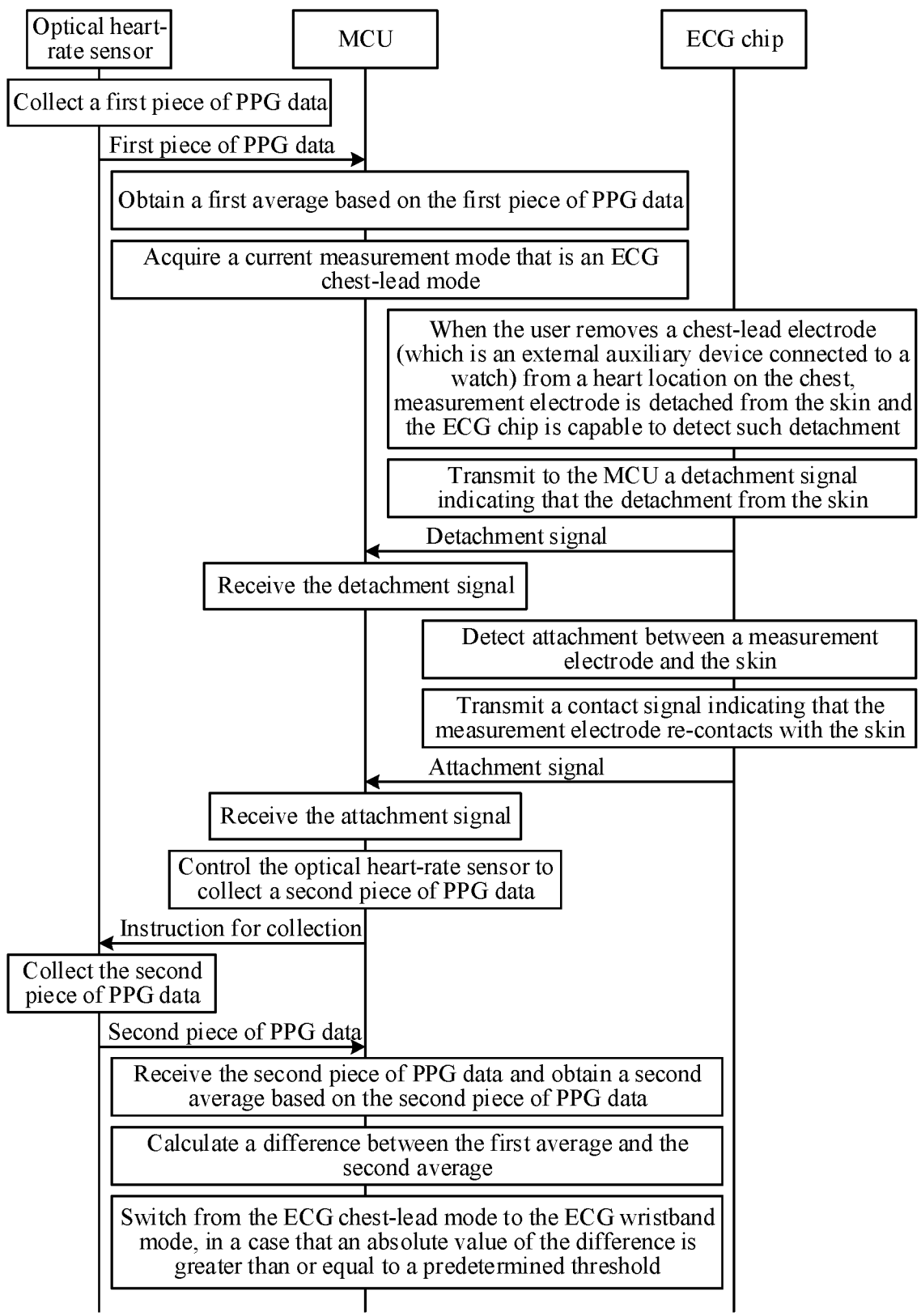
FIG. 4 is a flowchart of switching from an ECG chest-lead mode to the ECG wristband mode according to an embodiment of the present disclosure.

A method for switching from the ECG chest-lead mode to the ECG wristband mode is provided according to an embodiment of the present disclosure. Reference is made to FIG. 4, which is a flowchart of switching from an ECG chest-lead mode to an ECG wristband mode according to an embodiment of the present disclosure. The switching includes following steps.

In a case that a current measurement mode is the ECG chest-lead mode, the optical heart-rate sensor collects the preceding piece of the PPG data, and transmits the preceding piece of the PPG data to the MCU. The MCU obtains an average based on such piece of the PPG data, and further obtains the current measurement mode being the ECG chest-lead mode, due to previous storage of the current measurement mode. When a user removes a chest-lead electrode from (an external auxiliary device connected to a case of the watch) from the chest, a measurement electrode is detached from the skin, and the ECG chip detects such detachment (a bioelectric potential sensor on the chip detects no electrical signal after the measurement electrode is detached from the skin, that is, there is no data). Then, the ECG chip transmits to the MCU a detachment signal indicating the detachment from skin. When the watch is pressed against the wrist, the ECG chip detects that a measurement electrode is attached to the skin, and the ECG chip transmits to the MCU an attachment signal indicating such re-attachment to the skin. The MCU controls the optical heart-rate sensor to collect the succeeding piece of the PPG data. The MCU receives the succeeding piece of the PPG data and calculates a corresponding average. A difference between the average obtained after the re-attachment and the previously acquired average is calculated. In a case that the absolute value of such difference is greater than the predetermined threshold, the measurement mode is switched to the ECG wristband mode, and the ECG wristband mode is stored as the current measurement mode.

Figure 5:
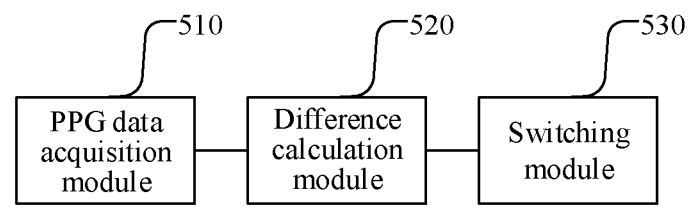
FIG. 5 is a schematic structural diagram of an apparatus for switching an ECG measurement mode according to an embodiment of the present disclosure.

Hereinafter illustrated is an apparatus for switching an ECG measurement mode according to an embodiment of the present disclosure. Description of the apparatus for switching an ECG measurement mode may refer to that of the forgoing method for switching the ECG measurement mode. Relevant modules are arranged in an MCU. Reference is made to FIG. 5, which is a schematic structural diagram of an apparatus for switching an ECG measurement mode according to an embodiment of the present disclosure. The apparatus includes a PPG data acquisition module 510, a difference calculation module 520, and a switching module 530.

The PPG data acquisition module 510 is configured to receive two successive pieces of PPG data transmitted by an optical heart-rate sensor, where the PPG data is generated by a contact between a measurement electrode and a skin.

The difference calculation module 520 is configured to calculate a difference between the two received pieces of the PPG data.

The switching module 530 is configured to control switching among measurement modes based on the difference. The measurement modes include an ECG wristband mode and an ECG chest-lead mode.

In some specific embodiments, the apparatus further includes a determination module. The determination module is configured to determine whether an absolute value of the difference is greater than or equal to a predetermined threshold.

In some specific embodiments, the PPG data acquisition module 510 includes a contact-state measuring unit and a PPG data acquisition unit.

The contact-state measuring unit is configured to detect, via an ECG chip, a state of the contact between the measurement electrode and the skin.

The PPG data acquisition unit is configured to obtain, based on the state of the contact, the two successive pieces of the PPG data transmitted by the optical heart-rate sensor.

In some specific embodiments, the difference calculation module 520 includes an average acquisition unit and a difference calculation unit.

The average acquisition unit is configured to obtain two averages based on the two received pieces, respectively, of the PPG data.

The difference calculation unit is configured to calculate the difference between the two averages as the difference between the two pieces of the PPG data.

In some specific embodiments, the PPG data acquisition module 510 includes a determination unit, a first PPG data acquisition unit, and a second PPG data acquisition unit.

The determination unit is configured to determine whether a piece of the PPG data being collected when the measurement electrode is detached from the skin is complete.

The first PPG data acquisition unit is configured to determine a piece of the PPG data received before the measurement electrode is detached from the skin as the preceding one of the two pieces of the PPG data, in response to the piece of the PPG data being collected when the measurement electrode is detached from the skin being not complete.

The second PPG data acquisition unit is configured to acquire the succeeding one of the two pieces of the PPG data when the measurement electrode is re-attached to the skin.

In some embodiments, the apparatus further includes a prompt module.

The prompt module is configured to transmit a current one of the measurement modes to a display device, to prompt a user that the switching is completed.

Embodiments of the apparatus for switching the ECG measurement mode correspond to those of the method for switching the ECG measurement mode. Therefore, description of the apparatus embodiments may refer to that of the method embodiments, and details are not repeated herein.

Figure 6:
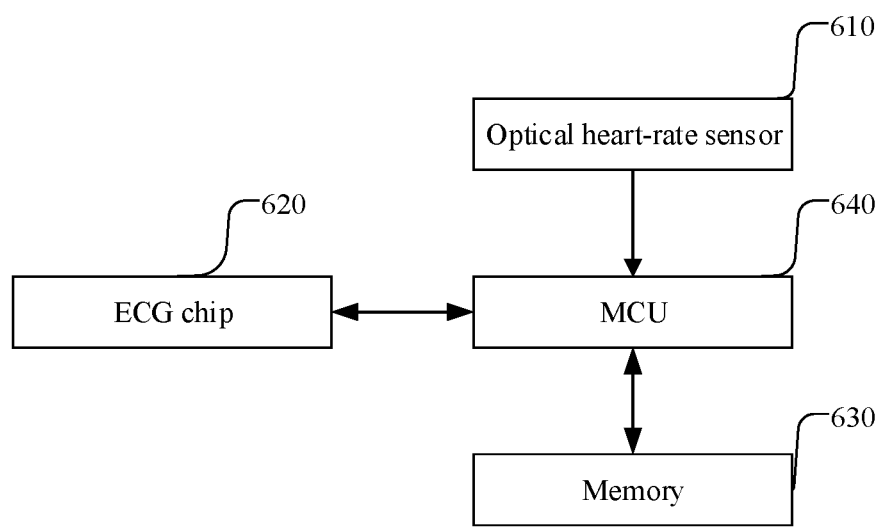
FIG. 6 is a schematic structural diagram of a wearable device according to an embodiment of the present disclosure.

Hereinafter illustrated is a wearable device according to an embodiment of the present disclosure. The wearable device may refer to the foregoing method for switching the ECG measurement mode. Reference is made to FIG. 6, which is a schematic structural diagram of a wearable device according to an embodiment of the present disclosure. The wearable device includes an optical heart-rate sensor 610, an ECG chip 620, a memory 630 and an MCU 640.

The optical heart-rate sensor 610 is configured to collect, at a preset sampling frequency, two successive pieces of PPG data generated by a contact between a measurement electrode and a skin.

The ECG chip 620 is configured to measure electrophysiological signals in an ECG wristband mode and in an ECG chest-lead mode, to monitor a heart rate.

The memory 630 is configured to store a computer program.

The MCU 640 is configured to perform the forgoing method for switching the ECG measurement mode when executing the computer program.

In an optional embodiment, the ECG chip 620 is further configured to transmit a detachment signal to the MCU, in response to detecting an electrical signal indicating that the measurement electrode is detached from the skin; and transmit an attachment signal to the MCU, in response to detecting an electrical signal indicating that the measurement electrode is re-attached to the skin.

Embodiments of the wearable device correspond to those of the method for switching the ECG measurement mode. Therefore, description of the device embodiments may refer to that of the method embodiments, and details are not repeated herein.

Hereinafter illustrate is a computer-readable storage medium according to an embodiment of the present disclosure. Description of the computer-readable storage medium corresponds to that of the foregoing method for switching an ECG measurement mode.

A computer-readable storage medium is provided according to an embodiment. The computer-readable storage medium stores a computer program that, when executed by a processor, implements steps of the foregoing method for switching an ECG measurement mode.

Embodiments of the computer-readable storage medium correspond to those of the method for switching the ECG measurement mode. Therefore, description of the medium embodiments may refer to that of the method embodiments, and details are not repeated herein.

The embodiments of the present disclosure are described in a progressive manner, and each embodiment places emphasis on the difference from other embodiments. Therefore, one embodiment can refer to other embodiments for the same or similar parts. Since the apparatuses disclosed in the embodiments correspond to the methods disclosed in the embodiments, the description of the apparatuses is simple, and reference may be made to the relevant part of the methods.

As further be appreciated by those skilled in the art, the units and algorithmic steps in the examples described according to the embodiments disclosed herein can be implemented in forms of electronic hardware, computer software or the combination of the both. To illustrate the interchangeability of the hardware and the software clearly, the components and the steps in the examples are described generally according to functions in the above description. Whether hardware or software is used to implement the functions depends on a specific application and design constraints for the technical solution. For each specific application, different methods may be used by those skilled in the art to implement the described function, and such implementation should not be considered to depart from the scope of this invention.

The steps of the method or algorithm described according to the embodiments disclosed herein can be implemented in forms of hardware, a software module executed by a processor or the combination of the both. The software module may be stored in a Random Access Memory (RAM), a memory, a Read-Only Memory (ROM), an electrically programmable ROM, an electrically erasable programmable ROM, a register, a hardware disk, a movable magnetic disk, CD-ROM or any other forms of storage medium well known in the art.

Hereinabove the method and the apparatus for switching the ECG measurement mode, the wearable device, and the computer-readable storage medium are illustrated in detail according to embodiments of the present disclosure. Specific examples are used to explain the principle and the embodiments of the present disclosure, and the forgoing description of the embodiments are only intended to help understand the method and the core idea of the present disclosure. Those skilled in the art may make various improvements and modifications to the present disclosure without departing from the principle of the present disclosure, and such improvements and modifications shall fall within the protection scope of the claims of the present disclosure.

The embodiments of the present disclosure are described in a progressive manner, and each embodiment places emphasis on the difference from other embodiments. Therefore, one embodiment can refer to other embodiments for the same or similar parts. Since the apparatuses disclosed in the embodiments correspond to the methods disclosed in the embodiments, the description of the apparatuses is simple, and reference may be made to the relevant part of the methods.

As further be appreciated by those skilled in the art, the units and algorithmic steps in the examples described according to the embodiments disclosed herein can be implemented in forms of electronic hardware, computer software or the combination of the both. To illustrate the interchangeability of the hardware and the software clearly, the components and the steps in the examples are described generally according to functions in the above description. Whether hardware or software is used to implement the functions depends on a specific application and design constraints for the technical solution. For each specific application, different methods may be used by those skilled in the art to implement the described function, and such implementation should not be considered to depart from the scope of this invention.

The steps of the method or algorithm described according to the embodiments disclosed herein can be implemented in forms of hardware, a software module executed by a processor or the combination of the both. The software module may be stored in a Random Access Memory (RAM), a memory, a Read-Only Memory (ROM), an electrically programmable ROM, an electrically erasable programmable ROM, a register, a hardware disk, a movable magnetic disk, CD-ROM or any other forms of storage medium well known in the art.

It should be noted that, the relationship terms such as "first", "second" and the like are only used herein to distinguish one entity or operation from another, rather than to necessitate or imply that an actual relationship or order exists between the entities or operations. Furthermore, the terms such as "include", "comprise" or any other variants thereof means to be non-exclusive. Therefore, a process, a method, an article or a device including a series of elements include not only the disclosed elements but also other elements that are not clearly enumerated, or further include inherent elements of the process, the method, the article or the device. Unless expressively limited, the statement "including a . . . " does not exclude the case that other similar elements may exist in the process, the method, the article or the device other than enumerated elements.

The invention claimed is:

1. A method for switching an electrocardiogram (ECG) measurement mode, comprising:
   receiving, by an ECG device, two pieces of photoplethysmography (PPG) data transmitted by an optical heart-rate sensor, wherein the PPG data is generated through the optical heart-rate sensor sensing a skin in contact with an ECG measurement electrode, and the two pieces of the PPG data are temporally successive among a plurality of pieces of the PPG data transmitted by the optical heart-rate sensor;
   calculating, by the ECG device, a difference between the two temporally successive pieces of the PPG data;
   switching, by the ECG device, the ECG device from a first measurement mode to a second measurement mode in response to the difference satisfying a preset condition;
   measuring, by the ECG device, electrophysiological signals for an ECG lead corresponding to a first part of a body, in response to the ECG device being in the first measurement mode; and
   measuring, by the ECG device, electrophysiological signals for an ECG lead corresponding to a second part of the body, in response to the ECG device being in the second measurement mode, wherein the first part is different from the second part.

2. The method according to claim 1, wherein:
   the preset condition is an absolute value of the difference being greater than or equal to a predetermined threshold.

3. The method according to claim 1, wherein receiving the two successive pieces of the PPG data transmitted by the optical heart-rate sensor comprises:
   detecting, via an ECG chip, a state of the contact between the ECG measurement electrode and the skin; and
   obtaining, based on the state of the contact, the two successive pieces of the PPG data transmitted by the optical heart-rate sensor.

4. The method according to claim 3, wherein calculating the difference between the two received pieces of the PPG data comprises:
   obtaining two averages based on the two received pieces, respectively, of the PPG data; and
   calculating a difference between the two averages as the difference between the two pieces of the PPG data.

5. The method according to claim 4, wherein obtaining, based on the state of contact, the two successive pieces of the PPG data transmitted by the optical heart-rate sensor comprises:
   determining whether a piece of the PPG data being collected when the ECG measurement electrode is detached from the skin is complete;
   determining a piece of the PPG data received before the ECG measurement electrode is detached from the skin as a preceding one of the two pieces of the PPG data, in response to the piece of the PPG data being collected when the ECG measurement electrode is detached from the skin being not complete; and
   acquiring a succeeding one of the two pieces of the PPG data when the ECG measurement electrode is re-attached to the skin.

6. The method according to claim 1, wherein after switching the ECG device from the first measurement mode to the second measurement mode, the method further comprises:
   transmitting a signal indicating the second measurement mode to a display device, to prompt a user that the switching is completed.

7. A computer-readable storage medium, wherein the computer-readable storage medium stores a computer program that, when executed by a processor, performs the method according to claim 1.

8. The method according to claim 1, wherein:
   the first measurement mode is a wristband mode, and the second measurement mode is a chest-lead mode; or
   the first measurement mode is a chest-lead mode, and the second measurement mode is a wristband mode.

9. An apparatus for switching an electrocardiogram (ECG) measurement mode, comprising:
   a memory, configured to store a computer program; and
   a processor, wherein the processor when executing the computer program is configured to perform:
      receiving two pieces of photoplethysmography (PPG) data transmitted by an optical heart-rate sensor, wherein the PPG data is generated through the optical heart-rate sensor sensing a skin in contact with an ECG measurement electrode, and the two pieces of the PPG data are temporally successive among a plurality of pieces of the PPG data transmitted by the optical heart-rate sensor;
   calculating a difference between the two temporally successive pieces of the PPG data;
   switching an ECG device, comprising the apparatus, from a first measurement mode to a second measurement mode in response to the difference satisfying a preset condition;
   instructing an ECG chip of the ECG device to measure electrophysiological signal for an ECG lead corresponding to a first part of a body, in response to the ECG device being in the first measurement mode; and
   instructing the ECG chip to measure electrophysiological signals for an ECG lead is corresponding to a second part of the body, in response to the ECG device being in the second measurement mode, wherein the first part is different from the second part.

10. The apparatus according to claim 9, wherein:
    the preset condition is an absolute value of the difference being greater than or equal to a predetermined threshold.

11. The apparatus according to claim 9, wherein receiving the two successive pieces of the PPG data transmitted by the optical heart-rate sensor comprises: detecting, via the ECG chip, a state of the contact between the ECG measurement electrode and the skin; and obtaining, based on the state of the contact, the two successive pieces of the PPG data transmitted by the optical heart-rate sensor.

12. The apparatus according to claim 11, wherein calculating the difference between the two received pieces of the PPG data comprises:
    obtaining two averages based on the two received pieces, respectively, of the PPG data; and
    calculating a difference between the two averages as the difference between the two pieces of the PPG data.

13. The apparatus according to claim 12, wherein obtaining, based on the state of contact, the two successive pieces of the PPG data transmitted by the optical heart-rate sensor comprises:

determining whether a piece of the PPG data being collected when the ECG measurement electrode is detached from the skin is complete;

determining a piece of the PPG data received before the ECG measurement electrode is detached from the skin as a preceding one of the two pieces of the PPG data, in response to the piece of the PPG data being collected when the ECG measurement electrode is detached from the skin being not complete; and acquiring a succeeding one of the two pieces of the PPG data when the ECG measurement electrode is re-attached to the skin.

14. The apparatus according to claim 9, wherein after switching the ECG device from the first measurement mode to the second measurement mode, the method further comprises:

transmitting a signal indicating the second measurement mode to a display device, to prompt a user that the switching is completed.

15. The apparatus according to claim 9, wherein:
the first measurement mode is a wristband mode, and the second measurement mode is a chest-lead mode; or
the first measurement mode is a chest-lead mode, and the second measurement mode is a wristband mode.

16. A wearable device, comprising:
the apparatus according to claim 7;
the optical heart-rate sensor, configured to collect the plurality of pieces of the PPG data at a preset sampling frequency; and
the ECG chip;
wherein the wearable device is the ECG device.

17. The wearable device according to claim 16, wherein the ECG chip is further configured to:

transmit a detachment signal to the apparatus, in response to detecting an electrical signal indicating that the ECG measurement electrode is detached from the skin; and transmit an attachment signal to the apparatus, in response to detecting an electrical signal indicating that the ECG measurement electrode is re-attached to the skin.

* * * * *